United States Patent
Schaeffer et al.

(10) Patent No.: US 7,708,931 B2
(45) Date of Patent: May 4, 2010

(54) BALLOON CATHETER

(75) Inventors: Darin G. Schaeffer, Bloomington, IN (US); David G. Burton, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 190 days.

(21) Appl. No.: 11/858,658

(22) Filed: Sep. 20, 2007

(65) Prior Publication Data

US 2008/0086084 A1 Apr. 10, 2008

Related U.S. Application Data

(60) Provisional application No. 60/850,235, filed on Oct. 5, 2006.

(51) Int. Cl.
*B29C 49/00* (2006.01)
*B29C 49/64* (2006.01)
*B29C 49/76* (2006.01)

(52) U.S. Cl. .................. 264/516; 264/520; 264/529; 264/534; 264/567

(58) Field of Classification Search .................. None
See application file for complete search history.

(56) References Cited

U.S. PATENT DOCUMENTS

| 4,251,305 | A | 2/1981 | Becker et al. ................ 156/86 |
| 5,002,559 | A | 3/1991 | Tower ........................ 606/194 |
| 5,087,394 | A | 2/1992 | Keith ........................... 204/22 |
| 5,499,973 | A | 3/1996 | Saab ............................ 604/96 |
| 5,807,520 | A | 9/1998 | Wang et al. ................ 264/520 |
| 5,846,238 | A | 12/1998 | Jackson et al. ............... 606/41 |
| 5,863,366 | A | 1/1999 | Snow ......................... 156/143 |
| 2004/0256049 | A1 | 12/2004 | O'Shaughnessy et al. ... 156/157 |

*Primary Examiner*—Monica A Huson
(74) *Attorney, Agent, or Firm*—Brinks Hofer Gilson & Lione

(57) ABSTRACT

An balloon catheter is provided with an improved neck portion. The neck portion of the balloon is used to attach the end of the balloon to a catheter. Before attaching the balloon to the catheter, the neck portion is lengthened and thinned out to make the neck portion more flexible. Heat shrink tubing may be used to apply pressure to the neck portion to force the material of the neck portion to flow along a mandrel inserted into the neck portion.

24 Claims, 2 Drawing Sheets

BALLOON CATHETER

This application claims priority to U.S. Provisional Application No. 60/850,235 filed Oct. 5, 2006, which is hereby incorporated by reference herein.

BACKGROUND

The present invention relates generally to medical devices and more particularly to intraluminal balloon catheters.

Balloon catheters are widely used in the medical profession for various intraluminal procedures. One common procedure involving the use of a balloon catheter relates to angioplasty dilation of coronary and other arteries suffering from stenosis (i.e., a narrowing of the arterial lumen that restricts blood flow). Angioplasty procedures have become a popular alternative to traditional procedures for treating stenoses because angioplasty procedures are considerably less invasive than other alternatives. For example, stenosis of the coronary arteries has traditionally been treated by performing bypass surgery. In general, bypass surgery involves splitting the chest bone to open the chest cavity and grafting a replacement vessel onto the heart to bypass the blocked, or stenosed, artery. However, coronary bypass surgery is a very invasive procedure that is risky and requires a long recovery time for the patient. Angioplasty procedures are also useful for treating stenoses in other regions of the vasculature as well, such as the carotid, brachial, renal, iliac and femoral arteries. In addition, angioplasty may be used to treat other vessels and passageways in the body.

Typically, angioplasty procedures are performed using a balloon-tipped catheter that may or may not have a balloon-expandable stent mounted on the balloon. In general, a physician performs an angioplasty procedure by introducing a balloon catheter into a peripheral artery (commonly one of the leg arteries) and threading the catheter to the narrowed region of the artery. During this stage, the balloon is uninflated and collapsed onto the shaft of the catheter in order to present a low profile which may be passed through the arterial lumens. Once the balloon is positioned at the narrowed region of the artery, the balloon is expanded by pumping a mixture of saline and contrast solution through the catheter to the balloon. As a result, the balloon presses against the inner wall of the artery to dilate it. If a balloon-expandable stent is mounted on the balloon, the balloon inflation also serves to expand the stent and implant it in the artery. After the artery is dilated, the balloon is deflated so that it once again collapses onto the shaft of the catheter. The balloon-tipped catheter is then retracted from the arteries. If a stent is mounted on the balloon of the catheter, the stent is left permanently implanted in its expanded state at the desired location in the artery to provide a support structure that prevents the artery from collapsing back to its pre-dilated condition. Alternatively, the balloon catheter may be used to dilate a stenosis without implanting a stent. A balloon-expandable stent or self-expandable stent may then be implanted in the dilated region in a follow-up procedure. If desired, a physician may also dilate the artery and stent a second time after the stent is implanted with a balloon catheter.

Although treatment of stenosed arteries in the vasculature is one common example where balloon catheters are used, this is only one example of how balloon catheters may be used and many other uses are possible. For example, balloon catheters may also be used to temporarily occlude vessels during medical procedures to prevent blood or other fluids from flowing through a vessel. Balloon catheters may also be used to expand other intraluminal devices without dilating the surrounding vessel wall, such as stent-grafts that may be used to treat aneurysms.

The above-described examples are only some of the applications in which balloon catheters are used by physicians. Many other applications for balloon catheters are known and/or may be developed in the future.

SUMMARY

A method of manufacturing a balloon catheter is described. A mandrel may be inserted through the neck portion of a balloon before the balloon is attached to a catheter. Heat shrink tubing is applied to the outside of the neck portion, and heat is applied to the heat shrink tube and the neck portion. As a result, the neck portion becomes longer and thinner. The mandrel may then be removed from the neck portion, and the neck portion and the catheter are attached to each other. One advantage of the improved neck portion is that the neck portion is more flexible and a smoother transition is achieved between the catheter and the balloon. Additional details and advantages are described below in the detailed description.

The invention may include any of the following aspects in various combinations and may also include any other aspect described below in the written description or in the attached drawings.

A method of manufacturing a balloon catheter, comprising:

molding a balloon into a shape comprising an inflatable portion and a neck portion;

inserting a mandrel through the neck portion;

applying a first heat shrink tubing onto an outer diameter of the neck portion;

heating the first heat shrink tubing and the neck portion thereby compressing the neck portion between the mandrel and the first heat shrink tubing and reducing a thickness of the neck portion;

removing the mandrel from the neck portion;

inserting a catheter through the neck portion; and bonding the neck portion to the catheter.

The method further comprising removing the first heat shrink tubing from the neck portion after heating the first heat shrink tubing.

The method further comprising sliding the first heat shrink tubing off the neck portion before removing the mandrel from the neck portion.

The method wherein the mandrel is inserted into the neck portion after the balloon is molded.

The method wherein the neck portion is bonded to the catheter by applying a second heat shrink tubing onto the outer diameter of the neck portion and heating the second heat shrink tubing, a contact region between the neck portion and the catheter thereby melting to bond the neck portion and the catheter.

The method further comprising:

removing the first heat shrink tubing from the neck portion after heating the first heat shrink tubing;

applying a second heat shrink tubing onto the outer diameter of the neck portion; and heating the second heat shrink tubing and the neck portion thereby compressing the neck portion between the mandrel and the second heat shrink tubing and reducing the thickness of the neck portion.

The method further comprising trimming a length of the neck portion after heating the first heat shrink tubing and before bonding the neck portion to the catheter.

The method wherein the molding the balloon comprises blow molding a polymer tube within a mold, and the balloon is removed from the mold before the mandrel is inserted through the neck portion.

The method wherein the neck portion comprises a length of less than 5 mm after the molding and the heating compresses the neck portion to increase the length at least 1 mm.

The method wherein the thickness of the neck portion is compressed to reduce the thickness at least 20%.

The method further comprising selecting one material to comprise the catheter and selecting a stiffer material to comprise the balloon.

The method wherein the mandrel is made from a Teflon material.

The method wherein the heat shrink tubing is made from FEP, RNF or TFE.

The method wherein an outer diameter of the mandrel is larger than an outer diameter of the catheter.

The method wherein the outer diameter of the mandrel is at least 0.001" larger than the outer diameter of the catheter.

The method wherein the molding the balloon comprises blow molding a polymer tube within a mold, and the balloon is removed from the mold before the mandrel is inserted through the neck portion, wherein the mandrel is inserted into the neck portion after the balloon is molded, and further comprising removing the first heat shrink tubing from the neck portion after heating the first heat shrink tubing.

The method further comprising sliding the first heat shrink tubing off the neck portion before removing the mandrel from the neck portion and trimming a length of the neck portion after heating the first heat shrink tubing and before bonding the neck portion to the catheter, wherein the neck portion is bonded to the catheter by applying a second heat shrink tubing onto the outer diameter of the neck portion and heating the second heat shrink tubing, a contact region between the neck portion and the catheter thereby melting to bond the neck portion and the catheter.

The method wherein the thickness of the neck portion is compressed to reduce the thickness at least 20%, further comprising selecting one material to comprise the catheter and selecting a stiffer material to comprise the balloon, and wherein an outer diameter of the mandrel is larger than an outer diameter of the catheter.

The method wherein the thickness of the neck portion is compressed to reduce the thickness at least 20%, further comprising removing the first heat shrink tubing from the neck portion after heating the first heat shrink tubing and selecting one material to comprise the catheter and selecting a stiffer material to comprise the balloon, wherein the neck portion is bonded to the catheter by applying a second heat shrink tubing onto the outer diameter of the neck portion and heating the second heat shrink tubing, a contact region between the neck portion and the catheter thereby melting to bond the neck portion and the catheter.

The method wherein the molding the balloon comprises blow molding a polymer tube within a mold, and the balloon is removed from the mold before the mandrel is inserted through the neck portion, further comprising removing the first heat shrink tubing from the neck portion after heating the first heat shrink tubing, applying a second heat shrink tubing onto the outer diameter of the neck portion, heating the second heat shrink tubing and the neck portion thereby compressing the neck portion between the mandrel and the second heat shrink tubing and reducing the thickness of the neck portion, and trimming a length of the neck portion after heating the first heat shrink tubing and before bonding the neck portion to the catheter, wherein the neck portion comprises a length of less than 5 mm after the molding and the heating steps compress the neck portion to increase the length at least 1 mm, and the neck portion is bonded to the catheter by applying a third heat shrink tubing onto the outer diameter of the neck portion and heating the third heat shrink tubing, a contact region between the neck portion and the catheter thereby melting to bond the neck portion and the catheter.

A balloon catheter manufactured by the process, comprising:

molding a balloon into a shape comprising an inflatable portion and a neck portion;

inserting a mandrel through the neck portion;

applying a first heat shrink tubing onto an outer diameter of the neck portion;

heating the first heat shrink tubing and the neck portion thereby compressing the neck portion between the mandrel and the first heat shrink tubing and reducing a thickness of the neck portion;

removing the mandrel from the neck portion;

inserting a catheter through the neck portion; and bonding the neck portion to the catheter.

BRIEF DESCRIPTION OF SEVERAL VIEWS OF THE DRAWINGS

The invention may be more fully understood by reading the following description in conjunction with the drawings, in which.

DETAILED DESCRIPTION

Figure 1:
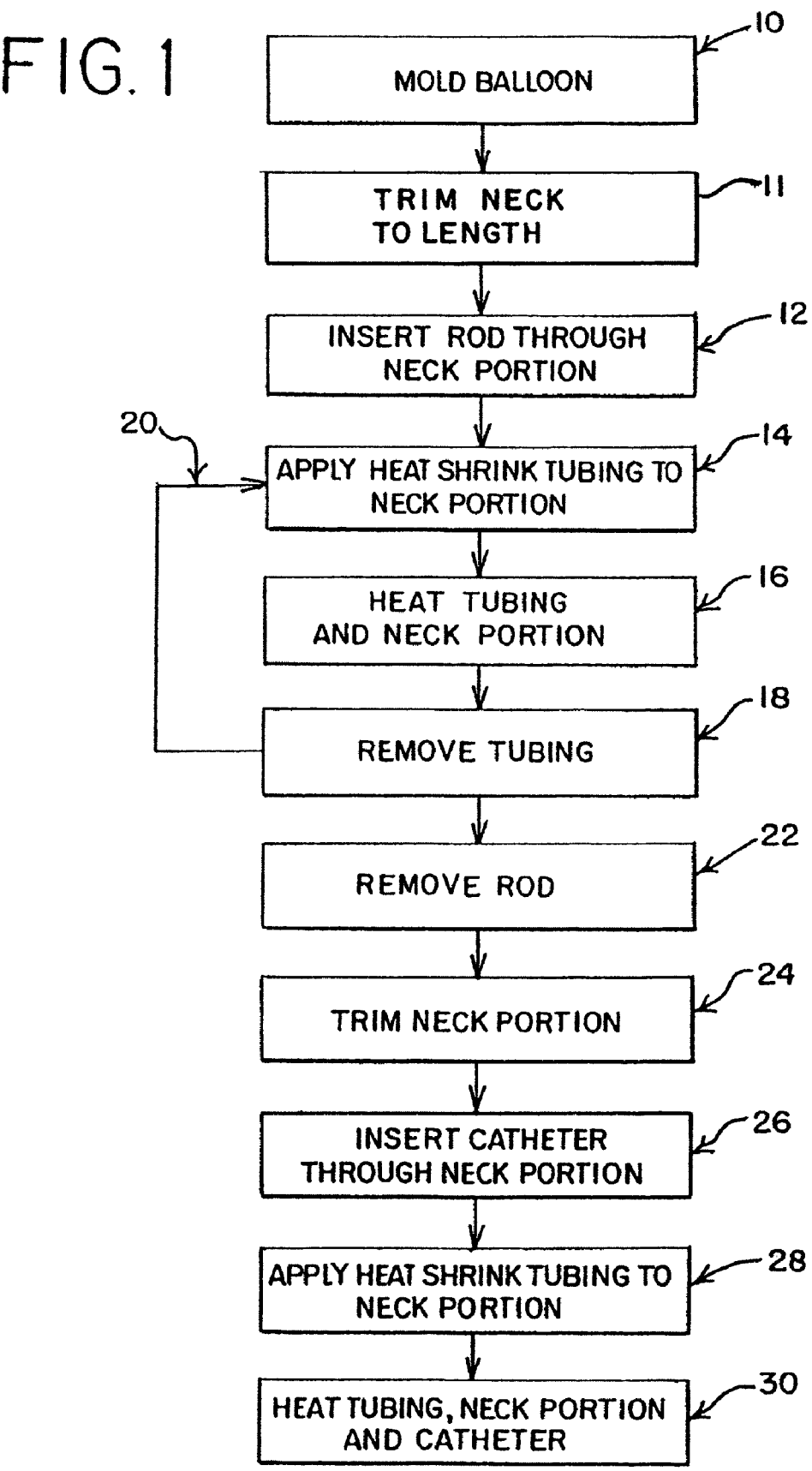
FIG. 1 is a flow chart showing steps that may be used to manufacture a balloon catheter.

Referring now to the drawings, a method of manufacturing an intraluminal balloon catheter is shown in FIG. 1. The balloon 32 used for the balloon catheter is preferably molded separately from the catheter using conventional techniques (10). Typically, a polymer tube is placed within a hollow mold shaped to correspond to the inflated configuration of the balloon. The polymer tube and/or mold is then heated and pressure is applied to the inner lumen of the tube to stretch and expand the polymer tube until the tube conforms to the shape of the mold.

Figure 2:
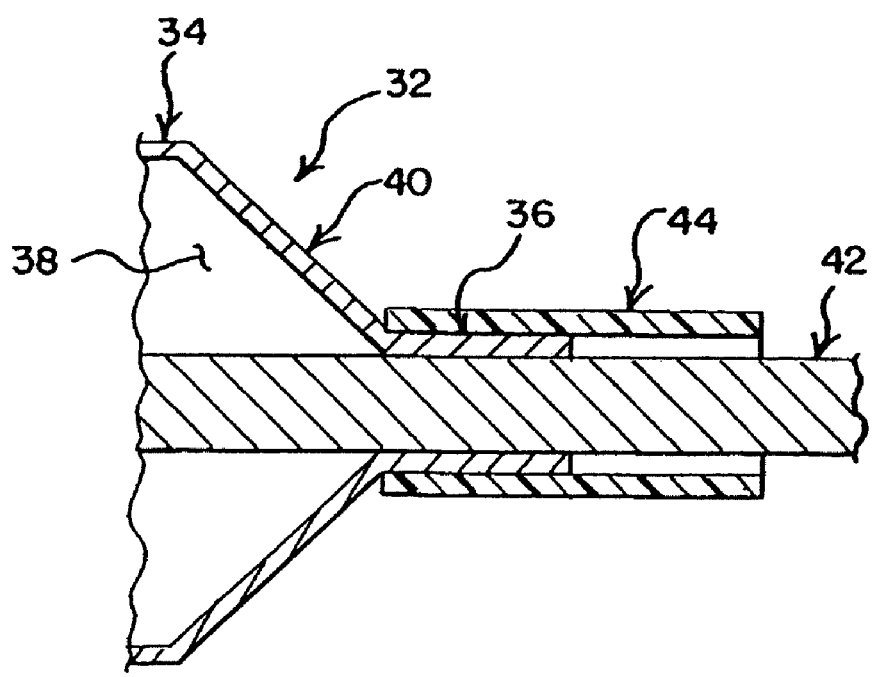
FIG. 2 is a cross-sectional view of a portion of a balloon mounted on a mandrel before the heat shrink tubing is heated.

As shown in FIG. 2, the molded balloon 32 generally includes an inflatable portion 34 with a larger outer diameter and a neck portion 36 with a smaller diameter. Although only one side of the balloon 32 is shown in FIG. 2, it is understood that the balloon 32 will generally have one neck portion 36 at the proximal end of the balloon 32 and another neck portion 36 at the distal end of the balloon 32. As understood by those skilled in the art, the inflatable portion 34 is adapted to inflate and deflate in response to an inflation medium that is fed to the interior region 38 of the balloon 32 when the balloon 32 is mounted on a catheter. The inflatable portion 34 may be cylindrical as shown or may have another shape suitable for particular medical procedures. As described below, the neck portion 36 is adapted to attach the balloon 32 to the catheter. The transition portion 40 connects the inflatable portion 34 and the neck portion 36 and is generally tapered therebetween. Although a variety of materials may be used, a typical material that may be used for the balloon 32 is nylon, PET or a PEBAX. Preferably, the balloon 32 has a diameter of about 5 mm or greater.

After the balloon 32 is molded, the shaped balloon 32 is removed from the mold. If the neck portions 36 of the balloon 32 are longer than desired after the molding step, the neck portions 36 may be trimmed to the desirable length (11). A mandrel 42 (also referred to as beading) may then be inserted through the neck portion 36 of the balloon 32 (12). Preferably, the mandrel 42 is made from a material that is relatively stiff with a high melting point. For example, Teflon, FEP or metal may be used to form the mandrel 42. The mandrel 42 may also be coated with Teflon or FEP. In addition, it is preferred that the diameter of the mandrel 42 is larger than the outer diameter of the catheter that the balloon 32 will be mounted on. For example, the diameter of the mandrel 42 may be at least 0.001" larger than the catheter so that inner diameter of the neck portion 36 easily slides onto the catheter after the mandrel 42 is removed from the neck portion 36.

Heat shrink tubing 44 is then applied to the neck portion 36 of the balloon 32 (14). Preferably, the heat shrink tubing 44 is slid coaxially over the neck portion 36 and the mandrel 42. A variety of well-known heat shrink tubes 44 may be used as desired. For example, one type of heat shrink tube 44 that may be used is FEP, RNF or TFE. Typically, the material properties of the heat shrink tubing 44 are designed to cause the tubing 44 to shrink when it is heated within a range of temperatures without melting.

Figure 3:
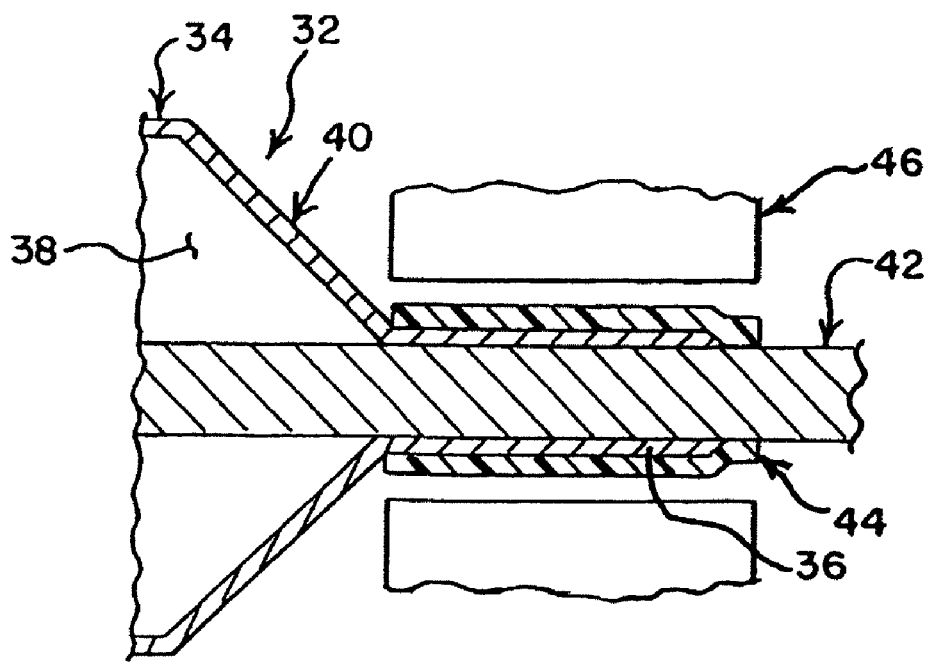
FIG. 3 is a cross-sectional view of the portion of the balloon mounted on the mandrel after the heat shrink tubing is heated.

In the preferred embodiment, the length of the neck portion 36 is initially between about 3 mm and 8 mm. Preferably, the initial length of the neck portion 36 is less than about 5 mm. The initial wall thickness of the neck portion 36 is preferably between about 0.005" and 0.012". Once the heat shrink tubing 44 is positioned over the neck portion 36, the heat shrink tubing 44 and the neck portion 36 are heated using conventional techniques (16). For example, conductive heat, a laser, induction heating or hot air from a heat gun may be used. As shown in FIG. 3, brass jaws 46 with a clam-like configuration may be used to radiate heat to the heat shrink tubing. Typically, the brass jaws 46 will include a heating element that heats the jaws, and the close proximity of the brass jaws 46 with the heat shrink tubing 44 causes the tubing 44 and the neck portion 36 to warm up. As the heat shrink tubing 44 is heated, the tubing 44 shrinks in diameter. As a result, the neck portion 36 is compressed between the heat shrink tubing 44 and the mandrel 42. Preferably, the heat also softens the material of the neck portion 36. This causes the neck portion 36 to flow along the length of the mandrel 42. Thus, the neck portion 36 of the balloon 32 increases in length and the wall thickness of the neck portion 36 becomes thinner. In the preferred embodiment, the length of the neck portion 36 increases by at least 1 mm. In addition, the thickness of the neck portion 36 is preferably reduced by at least 20% compared to the initial thickness of the neck portion 36.

The heat shrink tubing 44 may then be removed from the neck portion 36 after the heat shrink tubing 44 has lengthened and thinned the neck portion 36 (18). The heat shrink tubing 44 is typically removed by sliding the tubing 44 coaxially away from the neck portion 36. However, if it is desired to keep the heat shrink tubing 44 on the neck portion 36, the tubing 44 may be left on the neck portion 36 without removing the tubing 44. The heat shrink tubing 44 may also be removed later in the process. If it is desired to lengthen and thin the neck portion 36 further, another heat shrink tubing 44 can be applied to the neck portion 36 after the first heat shrink tubing 44 is removed (20). The heating step may then be repeated to compress the neck portion 36 a second time to cause it to lengthen and thin out further (20). Once the desired thickness or length of the neck portion 36 is achieved, the mandrel 42 may be removed from the neck portion 36 (22). If the length of the neck portion 36 is longer than desired, the neck portion 36 may be trimmed to the desired length (24). The neck portion 36 may also be trimmed while the neck portion 36 is mounted on the mandrel 42 before removing the mandrel 42.

Next, the catheter is inserted through the neck portion 36 (26). The catheter may be manufactured using conventional techniques. The catheter may be made up of one or more pieces and is generally adapted to be passed intraluminally through passageways in a body. The catheter may have reinforcing structures embedded within the catheter to provide the catheter with a particular rigidity and flexibility. For example, a helical wire may be embedded within the wall of the catheter if desired. The catheter may also have a guidewire lumen adapted to receive a guidewire to allow the catheter to be threaded over the guidewire to facilitate placement of the catheter within body passageways. The catheter may also include an inflation lumen in open communication with the interior region 38 of the balloon 32 to allow an inflation medium to pass to the balloon 32. If desired, various coatings may be applied to the catheter, such as a hydrophilic coating to make passage through body passageways less traumatic. In addition, the catheter may have a tapered distal tip to make the catheter atraumatic. The catheter may also have a manifold at the proximal end with ports that communicate with the lumens passing through the catheter.

In order to bond the balloon 32 to the catheter, another heat shrink tubing 44 may be applied to the neck portion 36 after the catheter is inserted through the neck portion 36 (28). The heat shrink tubing 44, neck portion 36 and catheter are then heated (30). As a result, the contact region between the neck portion 36 and the catheter melt to bond the neck portion 36 and catheter together. Preferably, the material selected for the catheter is softer than the material selected for the balloon 32. For example, the catheter may be made from Nylon or PEBAX. Preferably, the diameter of the catheter is between about 0.040" and 0.078". After the neck portion 36 and catheter are bonded together, the heat shrink tubing 44 may be removed from the neck portion 36. However, if desired, the heat shrink tubing 44 may be left on the neck portion 36 to provide a transition between the catheter and the balloon 32.

The advantages of the balloon catheter are now apparent. In general, conventional balloon catheters use a relatively stiff material for the balloon. This is typically necessary because high inflation pressures are needed to achieve the dilation forces that are usually desired to treat stenoses and accomplish other medical procedures. Stiff materials for the balloon are also desirable to prevent the balloon from rupturing during use. By contrast, relatively soft materials are desirable for the catheter. In general, a balloon catheter must usually pass through several passageways that may have tortuous bends before reaching the treatment site in the body. A soft catheter that is flexible is preferred so that threading the balloon catheter through the passageways is less difficult. A flexible catheter is also less traumatic to the passageways.

In conventional balloon catheters the neck portion of the balloon may increase the stiffness of the catheter along the bonded region between the neck portion and the catheter. As a result, conventional balloon catheters may be more difficult to thread through tortuous passageways since the bonded region at the neck portion is fairly rigid. By contrast, it may be easier to thread a balloon catheter with the improved neck portion through passageways with tight turns because the neck portion is more flexible. In addition, the neck portion may form a step between the catheter and the balloon. This is generally undesirable since the step may increase trauma to the vessel wall when the balloon catheter is threaded through or withdrawn from body passageways.

The method of manufacturing the balloon catheter described above improves the transition of the neck portion 36 by lengthening and/or thinning out the neck portion 36. As a result, the neck portion 36 that is bonded to the catheter is more flexible. The transition between the catheter and the balloon 32 also presents a smaller step. Thus, the described method provides a more flexible balloon catheter and a smoother transition between the catheter and the balloon 32. Another advantage is that the smooth transition between the catheter and the balloon 32 can be accomplished even though a relatively stiff material is selected for the balloon 32 and a relatively soft material is selected for the catheter. Because of the differences in stiffness between the balloon and the catheter, it is generally ineffective to try to form a smooth transition after the balloon has been mounted on the catheter. For example, heat shrink tubing could be applied to the neck portion after the catheter is inserted through the neck portion. However, when the heat shrink tubing is heated, the softer catheter material tends to melt and flow more than the stiffer neck portion. As a result, it is difficult to effectively thin out the neck portion after it has been mounted on a catheter. In addition, it is impractical to trim any excess length from the neck portion after the catheter is inserted through the neck portion.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

We claim:

1. A method of manufacturing a balloon catheter, comprising:
    molding a balloon into a shape comprising an inflatable portion and a neck portion, wherein said inflatable portion has a first diameter and said neck portion has a second diameter, said first diameter being larger than said second diameter, wherein said neck portion has a first thickness;
    inserting a mandrel through said neck portion, an outer surface of said mandrel being in direct contact with an inner surface of said neck portion;
    applying a first heat shrink tubing onto an outer diameter of said neck portion;
    heating said first heat shrink tubing and said neck portion thereby compressing said neck portion between said mandrel and said first heat shrink tubing, wherein said heating and compressing of said neck portion causes said neck portion to flow along said mandrel and lengthen said neck portion such that said first thickness is reduced to a second thickness;
    removing said mandrel from said neck portion after said first thickness has been reduced to said second thickness and prior to inserting a catheter through said neck portion;
    inserting said catheter through said neck portion having said reduced second thickness; and
    bonding said neck portion having said reduced second thickness to said catheter.

2. The method according to claim 1, further comprising removing said first heat shrink tubing from said neck portion after heating said first heat shrink tubing.

3. The method according to claim 2, further comprising sliding said first heat shrink tubing off said neck portion before removing said mandrel from said neck portion.

4. The method according to claim 1, wherein said mandrel is inserted into said neck portion after said balloon is molded.

5. The method according to claim 1, wherein said neck portion is bonded to said catheter by applying a second heat shrink tubing onto said outer diameter of said neck portion and heating said second heat shrink tubing, a contact region between said neck portion and said catheter thereby melting to bond said neck portion and said catheter.

6. The method according to claim 1, further comprising:
    removing said first heat shrink tubing from said neck portion having said second thickness after heating said first heat shrink tubing;
    applying a second heat shrink tubing onto said outer diameter of said neck portion; and
    heating said second heat shrink tubing and said neck portion having said second thickness thereby compressing said neck portion having said second thickness between said mandrel and said second heat shrink tubing, wherein said heating and compressing of said neck portion having said second thickness causes said neck portion to further flow along said mandrel and further lengthen said neck portion such that said second thickness is further reduced to a third thickness.

7. The method according to claim 1, further comprising trimming a length of said neck portion after heating said first heat shrink tubing and before bonding said neck portion to said catheter.

8. The method according to claim 1, wherein said molding said balloon comprises blow molding a polymer tube within a mold, and said balloon is removed from said mold before said mandrel is inserted through said neck portion.

9. The method according to claim 1, wherein said neck portion comprises a length of less than about 5 mm after said molding and said heating compresses said neck portion to increase said length at least 1 mm.

10. The method according to claim 1, wherein said second thickness of said neck portion is at least 20% thinner than said first thickness.

11. The method according to claim 1, further comprising selecting one material to comprise said catheter and selecting a different material that is stiffer than said one material to comprise said balloon.

12. The method according to claim 1, wherein said mandrel is made from a Teflon material.

13. The method according to claim 1, wherein said heat shrink tubing is made from FEP, RNF or TFE.

14. The method according to claim 1, wherein an outer diameter of said mandrel is larger than an outer diameter of said catheter.

15. The method according to claim 14, wherein said outer diameter of said mandrel is at least 0.001" larger than said outer diameter of said catheter.

16. The method according to claim 1, wherein said molding said balloon comprises blow molding a polymer tube within a mold, and said balloon is removed from said mold before said mandrel is inserted through said neck portion, wherein said mandrel is inserted into said neck portion after said balloon is molded, and further comprising removing said first heat shrink tubing from said neck portion after heating said first heat shrink tubing.

17. The method according to claim 16, further comprising sliding said first heat shrink tubing off said neck portion before removing said mandrel from said neck portion and trimming a length of said neck portion having said second thickness after heating said first heat shrink tubing and before bonding said neck portion to said catheter, wherein said neck portion having said second thickness is bonded to said catheter by applying a second heat shrink tubing onto said outer diameter of said neck portion and heating said second heat shrink tubing, a contact region between said neck portion and said catheter thereby melting to bond said neck portion and said catheter.

18. The method according to claim 17, wherein said second thickness of said neck portion is at least 20% thinner than said first thickness, and wherein said method further comprises selecting one material to comprise said catheter and selecting a different material that is stiffer than said one material to comprise said balloon, and wherein an outer diameter of said mandrel is larger than an outer diameter of said catheter.

19. The method according to claim 1, wherein said second thickness of said neck portion is at least 20% thinner than said first thickness, and wherein said method further comprising comprises removing said first heat shrink tubing from said neck portion after heating said first heat shrink tubing and selecting one material to comprise said catheter and selecting a different material that is stiffer than said one material comprising said balloon, wherein said neck portion is bonded to said catheter by applying a second heat shrink tubing onto said outer diameter of said neck portion having said second thickness and heating said second heat shrink tubing, a contact region between said neck portion having said second thickness and said catheter thereby melting to bond said neck portion and said catheter.

20. The method according to claim 1, wherein said molding said balloon comprises blow molding a polymer tube within a mold, and said balloon is removed from said mold before said mandrel is inserted through said neck portion, further comprising removing said first heat shrink tubing from said neck portion having said second thickness after heating said first heat shrink tubing, applying a second heat shrink tubing onto said outer diameter of said neck portion having said second thickness, heating said second heat shrink tubing and said neck portion having said second thickness thereby compressing said neck portion having said second thickness between said mandrel and said second heat shrink tubing, wherein said heating and compressing of said neck portion having said second thickness causes said neck portion to further flow along said mandrel and further lengthen said neck portion such that said second thickness is further reduced to a third thickness, said method further comprising and trimming a length of said neck portion after heating said first heat shrink tubing and before bonding said neck portion to said catheter, wherein said neck portion comprises a length of less than about 5 mm after said molding and said heating steps compress said neck portion to increase said length at least 1 mm, and said neck portion is bonded to said catheter by applying a third heat shrink tubing onto said outer diameter of said neck portion having said third thickness and heating said third heat shrink tubing, a contact region between said neck portion having said third thickness and said catheter thereby melting to bond said neck portion and said catheter.

21. A method of manufacturing a balloon catheter, comprising: molding a balloon into a shape comprising an inflatable portion and a neck portion;
inserting a mandrel through said neck portion;
applying a first heat shrink tubing onto an outer diameter of said neck portion;
heating said first heat shrink tubing and said neck portion thereby compressing said neck portion between said mandrel and said first heat shrink tubing and reducing a thickness of said neck portion;
removing said mandrel from said neck portion;
trimming a length of said neck portion after heating said first heat shrink tubing and before bonding said neck portion to said catheter;
inserting a catheter through said neck portion; and
bonding said neck portion to said catheter.

22. A method of manufacturing a balloon catheter, comprising: molding a balloon into a shape comprising an inflatable portion and a neck portion;
inserting a mandrel through said neck portion;
applying a first heat shrink tubing onto an outer diameter of said neck portion;
heating said first heat shrink tubing and said neck portion thereby compressing said neck portion between said mandrel and said first heat shrink tubing and reducing a thickness of said neck portion;
sliding said first heat shrink tubing off said neck portion before removing said mandrel from said neck portion;
removing said mandrel from said neck portion;
trimming a length of said neck portion after heating said first heat shrink tubing and before bonding said neck portion to said catheter;
inserting a catheter through said neck portion; and
bonding said neck portion to said catheter,
wherein said molding said balloon comprises blow molding a polymer tube within a mold, and said balloon is removed from said mold before said mandrel is inserted through said neck portion, wherein said mandrel is inserted into said neck portion after said balloon is molded, and further comprising removing said first heat shrink tubing from said neck portion after heating said first heat shrink tubing, and
wherein said neck portion is bonded to said catheter by applying a second heat shrink tubing onto said outer diameter of said neck portion and heating said second heat shrink tubing, a contact region between said neck portion and said catheter thereby melting to bond said neck portion and said catheter.

23. The method according to claim 22, wherein said thickness of said neck portion is compressed to reduce said thickness at least 20%, further comprising selecting one material to comprise said catheter and selecting a stiffer material to comprise said balloon, and wherein an outer diameter of said mandrel is larger than an outer diameter of said catheter.

24. A method of manufacturing a balloon catheter, comprising: molding a balloon into a shape comprising an inflatable portion and a neck portion;
inserting a mandrel through said neck portion;
applying a first heat shrink tubing onto an outer diameter of said neck portion;
heating said first heat shrink tubing and said neck portion thereby compressing said neck portion between said mandrel and said first heat shrink tubing and reducing a thickness of said neck portion;
removing said first heat shrink tubing from said neck portion after heating said first heat shrink tubing and applying a second heat shrink tubing onto said outer diameter of said neck portion;
heating said second heat shrink tubing and said neck portion thereby compressing said neck portion between said mandrel and said second heat shrink tubing and reducing said thickness of said neck portion;

removing said mandrel from said neck portion;

trimming a length of said neck portion after heating said first heat shrink tubing and before bonding said neck portion to said catheter;

inserting a catheter through said neck portion; and bonding said neck portion to said catheter, wherein said molding said balloon comprises blow molding a polymer tube within a mold, and said balloon is removed from said mold before said mandrel is inserted through said neck portion, and wherein said neck portion comprises a length of less than about 5 mm after said molding and said heating steps compress said neck portion to increase said length at least 1 mm, said neck portion being bonded to said catheter by applying a third heat shrink tubing onto said outer diameter of said neck portion and heating said third heat shrink tubing, a contact region between said neck portion and said catheter thereby melting to bond said neck portion and said catheter.

\* \* \* \* \*

UNITED STATES PATENT AND TRADEMARK OFFICE
CERTIFICATE OF CORRECTION

| | | |
|---|---|---|
| PATENT NO. | : 7,708,931 B2 | Page 1 of 1 |
| APPLICATION NO. | : 11/858658 | |
| DATED | : May 4, 2010 | |
| INVENTOR(S) | : Darin G. Schaeffer et al. | |

It is certified that error appears in the above-identified patent and that said Letters Patent is hereby corrected as shown below:

In the Claims

In column 9, claim 20, line 54, before "trimming a length", delete "and".

Signed and Sealed this

Sixth Day of July, 2010

David J. Kappos
*Director of the United States Patent and Trademark Office*